(12) United States Patent
Durden

(10) Patent No.: US 6,737,068 B2
(45) Date of Patent: May 18, 2004

(54) WIPE FORMULATION

(75) Inventor: Catherine Durden, Midland Park, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/968,200

(22) Filed: Oct. 1, 2001

(65) Prior Publication Data

US 2003/0072789 A1 Apr. 17, 2003

(51) Int. Cl.$^7$ .............. A61K 7/48; A61K 7/50; A61K 9/70; A61K 7/32; A61F 13/15
(52) U.S. Cl. .............. 424/401; 424/430; 424/443; 424/445; 424/484; 424/65; 424/725; 424/736; 424/744; 514/117; 514/817; 514/828; 514/887; 514/947; 514/967
(58) Field of Search .............. 424/401, 443, 424/445, 484, 65, 725, 736, 744, 430; 514/117, 817, 828, 887, 947, 967

(56) References Cited

U.S. PATENT DOCUMENTS

| | | | | |
|---|---|---|---|---|
| 2,565,887 | A | 8/1951 | Salfisberg | 206/56 |
| 3,414,927 | A | 12/1968 | Worcester | 15/104.93 |
| 3,786,615 | A | 1/1974 | Bauer | 53/21 FC |
| 4,309,469 | A | 1/1982 | Varona | 428/74 |
| 4,383,986 | A | 5/1983 | Dubash et al. | 424/25 |
| 4,692,374 | A | 9/1987 | Bouchette | 428/288 |
| 4,732,797 | A | 3/1988 | Johnson et al. | 428/74 |
| 4,737,405 | A | 4/1988 | Bouchette | 428/288 |
| 4,741,944 | A | 5/1988 | Jackson et al. | 428/152 |
| 4,772,501 | A | 9/1988 | Johnson et al. | 428/74 |
| 4,781,974 | A | 11/1988 | Bouchette et al. | 428/288 |
| 4,817,790 | A | 4/1989 | Porat et al. | 206/205 |
| 4,818,594 | A | 4/1989 | Albien et al. | 428/224 |
| 4,865,221 | A | 9/1989 | Jackson et al. | 221/48 |
| 4,904,524 | A | 2/1990 | Yoh | 428/311.3 |
| 4,941,995 | A | 7/1990 | Richards | 252/407 |
| 5,049,440 | A | 9/1991 | Bornhoeft, III et al. | 428/288 |
| 5,141,803 | A * | 8/1992 | Pregozen | 442/123 |
| 5,152,996 | A | 10/1992 | Corey et al. | 424/443 |
| 5,215,759 | A | 6/1993 | Mausner | 424/489 |
| 5,219,646 | A | 6/1993 | Gallagher et al. | 428/287 |
| 5,256,417 | A | 10/1993 | Koltisko | 424/402 |
| 5,439,682 | A | 8/1995 | Wivell et al. | 724/401 |
| 5,447,930 | A * | 9/1995 | Nayak | 514/239.2 |
| 5,507,968 | A | 4/1996 | Palaikis | 252/90 |
| 5,512,199 | A | 4/1996 | Khan et al. | 252/106 |
| 5,599,549 | A | 2/1997 | Wivell et al. | 424/401 |
| 5,629,081 | A | 5/1997 | Richards et al. | 442/96 |
| 5,635,469 | A | 6/1997 | Fowler et al. | 510/406 |
| 5,648,083 | A | 7/1997 | Blieszner et al. | 424/402 |
| 5,658,577 | A | 8/1997 | Fowler et al. | 424/401 |
| 5,665,364 | A | 9/1997 | McAtee et al. | 424/401 |
| 5,683,971 | A | 11/1997 | Rose et al. | 510/130 |
| 5,686,088 | A | 11/1997 | Mitra et al. | 424/404 |
| 5,686,089 | A | 11/1997 | Mitra et al. | 424/405 |
| 5,699,912 | A | 12/1997 | Ishikawa et al. | 206/494 |
| 5,702,992 | A | 12/1997 | Martin et al. | 442/123 |
| 5,716,625 | A | 2/1998 | Hahn et al. | 424/401 |
| 5,728,690 | A * | 3/1998 | Chen | 514/179 |
| 5,733,572 | A | 3/1998 | Unger et al. | 424/450 |
| 5,736,128 | A | 4/1998 | Chaudhuri et al. | 424/78.03 |
| 5,750,484 | A | 5/1998 | Falbaum et al. | 510/276 |
| 5,753,245 | A | 5/1998 | Fowler et al. | 424/401 |
| 5,753,246 | A | 5/1998 | Peters | 424/404 |
| 5,804,203 | A | 9/1998 | Hahn et al. | 424/402 |
| 5,897,856 | A * | 4/1999 | Trinh et al. | 424/65 |
| 5,908,617 | A | 6/1999 | Moore et al. | 424/70.19 |
| 5,915,394 | A | 6/1999 | Rickard | 132/333 |
| 5,939,050 | A | 8/1999 | Iyer et al. | 424/49 |
| 5,942,214 | A | 8/1999 | Lucas et al. | 424/65 |
| 5,962,399 | A | 10/1999 | Wulff et al. | 510/470 |
| 5,968,539 | A | 10/1999 | Beerse et al. | 424/405 |
| 5,993,792 | A | 11/1999 | Rath et al. | 424/70.28 |
| 6,001,344 | A | 12/1999 | Villa et al. | 424/78.02 |
| 6,007,799 | A | 12/1999 | Lee et al. | 424/65 |
| 6,015,547 | A | 1/2000 | Yam | 424/49 |
| 6,015,816 | A | 1/2000 | Kostyniak et al. | 514/299 |
| 6,033,679 | A | 3/2000 | Woo et al. | 424/401 |
| 6,042,839 | A | 3/2000 | Lahanas et al. | 424/401 |
| 6,048,836 | A | 4/2000 | Romano et al. | 510/490 |

OTHER PUBLICATIONS

Textbook of Organic Medicinal and Pharmaceutical Chemistry, Second Edition,' Edited by Wilson et al., 1954, p. 281–282.*

Wenninger et al., International Cosmetic Ingredient Dictionary and Handbook, Seventh Edition, vol. 2, The Cosmetic, Toiletry, and Fragrance Association, pp. 1637.*

* cited by examiner

*Primary Examiner*—Sreeni Padmanabhan
*Assistant Examiner*—Clinton Ostrup
(74) *Attorney, Agent, or Firm*—Ohlandt, Greeley, Ruggiero & Perle, LLP

(57) ABSTRACT

The present invention relates to a liquid formulation for a feminine wipe. The preferred formulation has an anti-irritant agent, a pH adjuster namely citric acid, and at least one preservative.

17 Claims, No Drawings

WIPE FORMULATION

BACKGROUND OF THE INVENTION

1. Field of the Invention

The present invention relates to a formulation for a wipe. More particularly, the present invention relates to a wipe or towelette formulation that has an anti-irritant agent. The wipe is particularly useful for feminine cleansing, and may alternatively be used for adult personal hygiene.

2. Description of the Prior Art

A towelette or wipe is generally an absorbent sheet that is treated or pre-moistened with a liquid formulation. The liquid used in pre-moistening the sheet is generally an aqueous solution. The solution may have a surface active detergent, a humectant and, in some instances, also a fragrance.

U.S. Pat. No. 5,804,203 to Hahn et al. is directed to a topical composition for reducing skin irritation in animals comprising an irritant ingredient and an anti-irritant amount of aqueous-soluble strontium cation.

U.S. Pat. No. 4,772,501 to Johnson et al. is directed to a wet wipe product having a fibrous wipe, a liquid preservative composition, and an enclosure for the fibrous wipe and the liquid preservative composition. The liquid preservative composition consists essentially of: (a) a mixture of citric acid and sorbic acid as the preservative component; (b) water; and (c) optional ingredients selected from the group consisting of skin moisturizers and fragrance compounds.

SUMMARY OF THE INVENTION

It is an object of the present invention to provide a mild formulation for use in a wipe.

It is another object of the present invention to provide a mild wipe formulation that has an anti-irritant agent.

It is a further object of the present invention to provide such a mild wipe formulation that prevents or minimizes skin irritation and itching especially feminine itching.

These and other objects and advantages of the present invention are achieved by a mild wipe formulation that comprises an anti-irritant agent, citric acid and at least one preservative. In one embodiment of the present invention, the wipe formulation comprises an anti-irritant agent, a pH adjuster, namely citric acid, at least one preservative, and one or more of the following: a humectant, a surfactant, a skin conditioning agent, an emulsifying agent, a chelating agent, a second preservative that specifically prevents mold, and a fragrance.

DETAILED DESCRIPTION OF THE INVENTION

The present invention is a liquid wipe formulation. This formulation is used primarily in a feminine wipe. The wipe formulation has an anti-irritant agent, a pH adjuster, namely citric acid, and at least one preservative.

The anti-irritant agent used in the present wipe formulation has been effective to clean, refresh and prevent further feminine itching. The anti-irritant agent is preferably one or more of the following: local anesthetics, analgesics, anesthetics, antipruitics, astringents, hydrocortisone preparations, keratolytics or any combinations thereof. The local anesthetics that can be used in the present invention include benzocaine, benzyl alcohol, dibucaine, dibucaine HCl, Dyclonine HCl, Lidocaine, Pramoxine HCl, Tetracaine, Tetracaine HCl, or any combinations thereof. The anti-irritant agent is preferably present in an amount from about 0.1 wt % up to about 50 wt % of the total weight of the liquid, wipe formulation. More preferably, the anti-irritant agent is preferably present in an amount about 9 wt % of the total weight of the liquid, wipe formulation.

When the anti-irritant agent is an anesthetic, it is preferably a mixture of the following local anesthetics, and preferably in the approximate amount, set forth below.

| Local Anesthetics in percentage by wt (wt %) of the wipe formulation | |
|---|---|
| Benzocaine | 5.0–20.0 |
| Benzyl alcohol | 1.0–4.0 |
| Dibucaine | 0.25–1.0 |
| Dibucaine HCl | 0.25–1.0 |
| Dyclonine HCl | 0.5–1.0 |
| Lidocaine | 2.0–5.0 |
| Pramoxine HCl | 1.0 |
| Tetracaine | 0.5–1.0 |
| Tetracaine HCl | 0.5–1.0 |

The analgesic, anesthetic or antipruitic anti-irritant agents that can be used in the present wipe formulation include camphor, juniper tar, menthol or combinations thereof. When the anti-irritant agent is an analgesic, an anesthetic or an antipruitic, it is preferably in the following mixture, and in an approximate range, set forth below.

| Analgesic, anesthetic and antipruitic in wt % of the wipe formulation | |
|---|---|
| Camphor | 0.1–3.0 |
| Juniper tar | 1.0–5.0 |
| Menthol | 0.1–1.0 |

The astringents that can be used in the present wipe formulation include calamine, zinc oxide or any combination thereof. When the anti-irritant agent is an astringent, it is preferably in the following mixture, and preferably in the approximate range, set forth below.

| Astringents in wt % of the wipe formulation | |
|---|---|
| Calamine | 5.0–25.0 |
| Zinc oxide | 5.0–25.0 |
| Witch hazel | 1.0–50.0 |

The hydrocortisone preparations that can be used in the present wipe formulation include hydrocortisone, hydrocortisone acetate or any combination thereof. If the anti-irritant agent is a hydrocortisone preparation, it is preferably present in the following mixture, and preferably in the approximate range, set forth below.

| Hydrocortisone preparations in wt % of the wipe formulation | |
| --- | --- |
| Hydrocortisone | 0.25–0.5 |
| Hydrocortisone acetate | 0.25–0.5 |

The keratolytics that can be used in the present wipe formulation include alcloxa, resorcinol or any combination thereof. When the anti-irritant agent is a keratolytic, it is preferably present the following mixture, and preferably in the approximate range, set forth below.

| Keratolytics in wt % of the wipe formulation | |
| --- | --- |
| Alcloxa | 0.2–2.0 |
| Resorcinol | 1.0–3.0 |

The second ingredient of the present wipe formulation is a pH adjuster. The preferred pH adjuster is citric acid. Preferably, citric acid is present in an amount from about 0.01 wt % to about 1 wt % of the total weight of the liquid, wipe formulation. More preferably, the citric acid is present in an amount from about 0.05 wt % to about 0.5 wt %, and most preferably about 0.1 wt %, of the total weight of the wipe formulation. With the above amounts of pH adjuster, the wipe formulation is in a pH range from about 4.0 to about 6.0, and preferably from about 4.5 to about 5.0.

The present wipe formulation has at least one preservative. That preservative is preferably one or more of the following: sodium hydroxymethylglycinate, polyaminopropyl biguanide, quaternary ammonium compound, EDTA salt, EDTA fatty acid conjugate, alkanol especially ethanol, isopropyl alcohol, benzyl alcohol, paraben, sorbate, urea derivative, and isothiazolinone, or any combination thereof. The preferred preservative is sodium hydroxymethylglycinate. The preservative is preferably present in an amount from about 0.2 wt % to about 2 wt %, and more preferably about 0.5 wt %, of the total weight of the wipe formulation.

In one embodiment of the present invention, the liquid wipe formulation has an anti-irritant agent, a pH adjuster, namely citric acid, and at least one preservative. In another embodiment of the present invention, the wipe formulation has the anti-irritant, the pH adjuster, namely citric acid, the at least one preservative, and one or more of the following ingredients: a humectant, a surfactant, a skin conditioning agent, an emulsifying agent, a chelating agent, a second preservative which specifically prevents mold, and a fragrance. In yet another embodiment of the present invention, the liquid wipe formulation includes the anti-irritant, the pH adjuster, namely citric acid, the at least one preservative, a humectant, a surfactant, a skin conditioning agent, an emulsifying agent, a chelating agent, a second preservative which specifically prevents mold, and a fragrance.

The humectant used in a wipe of the present invention is preferably one or more of the following: glycerol, propylene glycol, sorbitol urea, amino acid, polyol and other compounds with hygroscopic properties, or any combination thereof. The preferred humectant is propylene glycol. The humectant is preferably present in an amount from about 0.1 wt % up to about 2 wt % of the total weight of the liquid, wipe formulation. More preferably, the humectant is present in an amount about 0.5 wt %.

The surfactant that can be used in a wipe formulation of the present invention is preferably one or more of the following: alkylamido alkylamine, quaternary ammonium compound, phosphorus derivative, amphoteric imidazoline derivative, fatty sulfosuccinate ester and amide, ethoxylated sorbitan ester, betaine, alkoxylated alcohol, alkyl ether sulfate, disodium cocoamphodiacetate, cocamidopropyl betaine, PEG-80 glyceryl cocoate/PEG-30 glyceryl cocoate, decyl polyglucose, or any combinations thereof. The preferred surfactant is disodium cocoamphodiacetate. The surfactant is preferably present in an amount greater than about 0 to about 1 wt % of the total weight of the liquid, wipe formulation. More preferably, the surfactant is present in an amount about 0.10 wt % of the total weight of the wipe formulation.

The skin conditioning agent used in an embodiment of the present wipe formulation is preferably one or more of the following: botanical extract including aloe vera gel, ester including tocopherol acetate (vitamin E acetate), quaternary ammonium compound, asymmetrical carbonate, N-substituted carboxamide, urea or phosphine oxide, organic salt, or any combination thereof. The skin conditioning agent is preferably present in an amount greater than about 0 wt % up to about 1.25 wt % of the total weight of the liquid, wipe formulation. More preferably, it is present in an amount about 0.02 wt % of the wipe formulation. The preferred skin conditioning agents are aloe vera gel and tocopheryl acetate. When used, aloe vera gel is preferably present in an amount greater than about 0 to about 1 wt % of the total weight of the liquid formulation. More preferably, it is present in an amount about 0.01 wt %. When used, tocopheryl acetate (vitamin E acetate) is preferably present in an amount greater than about 0 to about 1.0 wt % of the total weight of the liquid formulation. More preferably, it is present in an amount about 0.01 wt % of the wipe formulation.

The emulsifying agent used in a wipe formulation of the present invention is any one or more of the following: sorbitan, alkoxylated fatty alcohol, alkylpolyglycoside, soap, alkyl sulfate, monoalkyl and dialkyl phosphate, alkyl sulphonate, acyl isothionate, or any combinations thereof. The preferred emulsifying agent is polysorbate 20. The emulsifying agent is preferably present in an amount greater than about 0 wt % to about 1 wt % of the total weight of the liquid, wipe formulation. More preferably, it is present in an amount about 0.25 wt % of the wipe formulation.

The chelating agent that can be used in a present wipe formulation is preferably one or more of the following: disodium EDTA (ethylenediamine tetraacetate), ethylenediamine-tetra-acetic acid, (ethylenedioxy)-diethylene-dinitrilo-tetra-acetic acid, salicylaldoxime, quinolinol, triethylenetetramine, or any combinations thereof. The preferred chelating agent is disodium EDTA. The chelating agent is preferably present in an amount greater than about 0 wt % up to about 0.2 wt % of the total weight of the liquid, wipe formulation. More preferably, the chelating agent is present in an amount about 0.1 wt % of the wipe formulation.

A wipe formulation of the present invention may include a second preservative that is specifically present to prevent mold. The preferred second preservative is potassium sorbate. The second preservative is preferably present in an amount from about 0.1 wt % to about 0.3 wt % of the total weight of the liquid, wipe formulation. More preferably, the second preservative is present in an amount about 0.14 wt % of the wipe formulation.

A wipe formulation of the present invention may include a fragrance. Any conventional fragrance that is mild and does not adversely affect sensitive areas for females, or other adults, may be used. Preferably, the fragrance is present in an amount greater than about 0 wt % up to about 0.5 wt %, and more preferably about 0.05 wt %, of the total weight of the liquid, wipe formulation.

The one example of the subject liquid wipe formulation is listed in Table 1 in weight percents, along with acceptable ranges.

TABLE 1

| Ingredient | Subject Formulation (wt %) | Ranges* (wt %) |
| --- | --- | --- |
| Water | QS | QS |
| Witch Hazel | 9 | 1–50 |
| Propylene Glycol | 0.5 | 0.1–2 |
| Disodium Cocoamphodiacetate | 0.1 | 0–1 |
| Tocopheryl Acetate (Vitamin E Acetate) | 0.01 | 0–1 |
| Aloe Vera Gel | 0.01 | 0–1 |
| Fragrance | 0.05 | 0–0.5 |
| Polysorbate 20 | 0.25 | 0–0.5 |
| Preservative | 0.5 | 0.2–2 |
| Disodium EDTA | 0.1 | 0–0.2 |
| Potassium Sorbate | 0.14 | 0.1–0.3 |
| Citric Acid | 0.1 | 0.01–1 |
| TOTAL | 100 | 100 |

The wipe formulations of the present invention have therapeutic benefits. In addition, they prevent or minimize skin irritation and itching. Moreover, each of the wipe formulations of the present invention is mild. The wipe formulations of the present invention may be used as a feminine wipe and, in particular, prevent or minimize feminine itching.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A liquid wipe or towellete formulation comprising an anti-irritant agent selected from the group consisting of analgesic, antipruitic, astringent, hydrocortisone preparation, keratolytic, and any combinations thereof; citric acid; and at least one preservative, wherein said at least one preservative is sodium hydroxymethylglycinate, and wherein the formulation is in a pH range from about 4.0 to about 6.0.

2. The formulation of claim 1, wherein said is at least one selected from the group consisting of witch hazel, calamine, zinc oxide, and any combinations thereof.

3. The formulation of claim 1, wherein said astringent is witch hazel.

4. The formulation of claim 1, further comprising a fragrance.

5. The formulation of claim 1, further comprising a humectant selected from the group consisting of glycerol, propylene glycol, sorbitol urea, amino acid, polyol, and any combinations thereof.

6. The formulation of claim 5, wherein said humectant is present in an amount from about 0.1 wt % to about 2 wt % of the total weight of the formulation.

7. The formulation of claim 1, further comprising a surfactant selected from the group consisting of alkylamido alkylamine, quaternary ammonium compound, phosphorus derivative, amphoteric imidazoline derivative, fatty sulfosuccinate ester and amide, ethoxylated sorbitan ester, betaine, alkoxylated alcohol, alkyl ether sulfate, disodium cocoamphodiacetate, cocamidopropyl betaine, PEG-80 glyceryl cocoate/PEG-30 glyceryl cocoate, decyl polyglucose, and any combinations thereof.

8. The formulation of claim 7, wherein said surfactant is present in an amount greater than about 0 wt % to about 1 wt % of the total weight of the formulation.

9. The formulation of claim 1, further comprising a skin conditioning agent selected from the group consisting of botanical extract, ester, quaternary ammonium compound, asymmetrical carbonate, N-substituted carboxamide, urea, phosphine oxide, organic salt, and any combinations thereof.

10. The formulation of claim 9, wherein the skin conditioning agent is in an amount greater than about 0 wt % up to about 1.25 wt % of the total weight of the formulation.

11. The formulation of claim 1, further comprising an emulsifying agent selected from the group consisting of: sorbitan, alkoxylated fatty alcohol, alkylpolyglycoside, soap, alkyl sulfate, monoalkyl and dialkyl phosphate, alkyl sulphonate, acyl isothionate, and any combinations thereof.

12. The formulation of claim 11, wherein the emulsifying agent is in an amount greater than about 0 wt % to about 1 wt % of the total weight of the formulation.

13. The formulation of claim 1, further comprising a chelating agent selected from the group consisting of disodium EDTA, ethylene-diamine-tetra-acetic acid, (ethylenedioxy)-diethlyene-dinitrilo-tetra-acetic acid, salicylaldoxime, quinolinol, triethylenetetramine, and any combinations thereof.

14. The formulation of claim 13, wherein said chelating agent is present in an amount greater than about 0 wt % up to about 0.2 wt % of the total weight of the formulation.

15. The formulation of claim 1, further comprising a second preservative that combats mold.

16. The formulation of claim 15, wherein said second preservative is in an amount from about 0.1 wt % to about 0.3 wt % of the total weight of the formulation.

17. The formulation of claim 15, wherein said second preservative is potassium sorbate.

* * * * *